(12) United States Patent
Heuft et al.

(10) Patent No.: US 8,283,659 B2
(45) Date of Patent: Oct. 9, 2012

(54) TETRAHYDROTETRAAZAPENTACENES IN THIN-FILM TRANSISTORS

(75) Inventors: Matthew A. Heuft, Oakville (CA); Yiliang Wu, Oakville (CA)

(73) Assignee: Xerox Corporation, Norwalk, CT (US)

( * ) Notice: Subject to any disclaimer, the term of this patent is extended or adjusted under 35 U.S.C. 154(b) by 138 days.

(21) Appl. No.: 12/977,209

(22) Filed: Dec. 23, 2010

(65) Prior Publication Data
US 2012/0161108 A1    Jun. 28, 2012

(51) Int. Cl.
*H01L 51/30* (2006.01)
(52) U.S. Cl. .............. 257/40; 257/59; 257/72
(58) Field of Classification Search .......... 257/40, 257/59–72, E51.02
See application file for complete search history.

(56) References Cited

U.S. PATENT DOCUMENTS

| 7,842,942 B2 * | 11/2010 | Brown et al. | 257/40 |
| 7,982,212 B2 * | 7/2011 | Suzuki et al. | 257/40 |
| 8,124,964 B2 * | 2/2012 | Takimiya et al. | 257/40 |
| 2009/0261321 A1 * | 10/2009 | Berens et al. | 257/40 |

* cited by examiner

*Primary Examiner* — Cuong Q Nguyen
(74) *Attorney, Agent, or Firm* — Fay Sharpe LLP (57) ABSTRACT

Compounds of Formula (I) are disclosed:

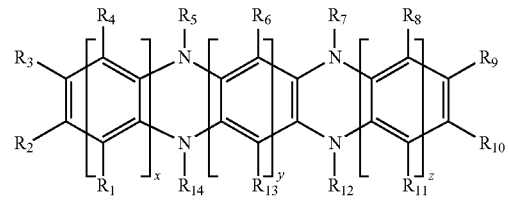

Formula (I)

wherein $R_1$-$R_{14}$, x, y, and z are as defined herein. The compounds are useful as semiconducting materials for electronic devices such as thin-film transistors.

20 Claims, 2 Drawing Sheets

TETRAHYDROTETRAAZAPENTACENES IN THIN-FILM TRANSISTORS

CROSS REFERENCE TO RELATED PATENTS AND APPLICATIONS

This application is related to U.S. patent application Ser. No. 12/977,187, filed concurrently. The disclosure of that application is hereby fully incorporated by reference herein.

BACKGROUND

The present disclosure relates to compounds known as tetrahydrotetrazaacenes, and derivatives thereof. These acenes are particularly useful as semiconductors in electronic devices, such as thin-film transistors. These acenes have improved performance characteristics.

Thin film transistors (TFTs) are fundamental components in modern-age electronics, including, for example, sensors, image scanners, memory devices, radio frequency identification tags, and electronic display devices. It is usually desired to make TFTs which have not only much lower manufacturing costs, but also appealing mechanical properties such as being physically compact, lightweight, flexible, and having enhanced performance characteristics. Organic thin film transistors (OTFTs) promise the above desired benefits.

OTFTs are generally composed of a supporting substrate, three electrically conductive electrodes (gate, source and drain electrodes), a channel semiconducting layer, and an electrically insulating gate dielectric layer separating the gate electrode from the semiconducting layer.

It is desirable to improve the performance of known OTFTs. One measure of performance is the charge carrier mobility of the semiconducting layer. The mobility is measured in units of $cm^2/V \cdot sec$; higher mobility is desired.

Most small organic semiconductors with high field-effect mobility are based on pentacene. However, pentacene has poor solubility, requiring an expensive high vacuum deposition process to be used. Soluble pentacene derivatives are prone to oxidation in solution when exposed to air, preventing device fabrication from solution in ambient conditions. There is a need to develop new technologies to dramatically improve the mobility for broad applications.

BRIEF DESCRIPTION

The present disclosure relates to tetrahydrotetraazaacenes which are useful as semiconductors or semiconducting materials. These acenes have high air stability both in the solid state and in solution, particularly when compared to pentacene. They can also be easily functionalized to change the resulting electronic, solubility, and oxidative stability properties.

Disclosed is a compound of Formula (I):

Formula (I)

wherein each $R_1$, $R_2$, $R_3$, $R_4$, $R_6$, $R_8$, $R_9$, $R_{10}$, $R_{11}$, and $R_{13}$ is independently selected from hydrogen, alkyl, alkenyl, alkynyl, substituted alkyl, substituted alkenyl, substituted alkynyl, aryl, substituted aryl, and halogen; each $R_5$, $R_7$, $R_{12}$, and $R_{14}$ is independently selected from hydrogen, alkyl, substituted alkyl, aryl, and substituted aryl; x is an integer from 1 to 3; y is an integer from 1 to 4; and z is an integer from 1 to 3.

In some embodiments, x, y, and z are 1 and $R_1$-$R_{14}$ are hydrogen.

In other embodiments, $R_2$ and $R_3$ are identical to each other, $R_9$ and $R_{10}$ are identical to each other, and $R_2$ is different from $R_9$.

Sometimes, $R_2$, $R_3$, $R_9$, and $R_{10}$ are not hydrogen.
In other versions, $R_2$, $R_3$, $R_9$, and $R_{10}$ are the same.
The compound may be of Formula (II):

Formula (II)

wherein $R_2$, $R_3$, $R_9$, and $R_{10}$, are independently selected from hydrogen, alkyl, alkenyl, alkynyl, substituted alkyl, substituted alkenyl, substituted alkynyl, aryl, substituted aryl, and halogen; wherein $R_5$, $R_7$, $R_{12}$, and $R_{14}$ are independently selected from hydrogen, alkyl, substituted alkyl, aryl, and substituted aryl; and wherein at least one of $R_2$, $R_3$, $R_5$, $R_7$, $R_9$, $R_{10}$, $R_{12}$, or $R_{14}$ is not hydrogen.

More specifically, the compound could be of Formula (III):

Formula (III)

wherein $R_2$, $R_3$, $R_9$, and $R_{10}$ are independently selected from hydrogen, alkyl, alkenyl, alkynyl, substituted alkyl, substituted alkenyl, substituted alkynyl, aryl, substituted aryl, and halogen; and wherein at least one of $R_2$, $R_3$, $R_9$, or $R_{10}$ is not hydrogen. In some versions of Formula (III), $R_2$ and $R_3$ are identical to each other, $R_9$ and $R_{10}$ are identical to each other, and $R_2$ is different from $R_9$.

Other times, the compound is of Formula (IV):

Formula (IV)

wherein $R_5$, $R_7$, $R_{12}$, and $R_{14}$ are independently selected from alkyl, substituted alkyl, aryl, and substituted aryl.

In specific versions of Formula (IV) $R_5$, $R_7$, $R_{12}$, and $R_{14}$ are the same. In other specific versions, $R_5$ and $R_{14}$ are identical to each other; $R_7$ and $R_{12}$ are identical to each other; and $R_5$ is different from $R_7$.

Also disclosed is a thin film transistor, comprising: a substrate; and a semiconducting layer on the substrate, the semiconducting layer comprising a tetrahydrotetraazaacene of Formula (I):

Formula (I)

wherein each $R_1$, $R_2$, $R_3$, $R_4$, $R_6$, $R_8$, $R_9$, $R_{10}$, $R_{11}$, and $R_{13}$ is independently selected from hydrogen, alkyl, alkenyl, alkynyl, substituted alkyl, substituted alkenyl, substituted alkynyl, aryl, substituted aryl, and halogen; each $R_5$, $R_7$, $R_{12}$, and $R_{14}$ is independently selected from hydrogen, alkyl, substituted alkyl, aryl, and substituted aryl; x is an integer from 1 to 3; y is an integer from 1 to 4; and z is an integer from 1 to 3.

Sometimes, x, y, and z are 1 and $R_1$-$R_{14}$ are hydrogen.

In some embodiments, x and z are equal to each other.

In other embodiments, y is from 2 to 4.

In further embodiments, $R_5$, $R_7$, $R_{12}$, and $R_{14}$ are the same.

In particular embodiments, $R_2$ and $R_3$ are identical to each other, $R_9$ and $R_{10}$ are identical to each other, and $R_2$ is different from $R_9$.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

A more complete understanding of the components, processes, and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10."

The present disclosure is related to compounds of Formula (I):

Formula (I)

wherein each $R_1$, $R_2$, $R_3$, $R_4$, $R_6$, $R_8$, $R_9$, $R_{10}$, $R_{11}$, and $R_{13}$ is independently selected from hydrogen, alkyl, alkenyl, alkynyl, substituted alkyl, substituted alkenyl, substituted alkynyl, aryl, substituted aryl, and halogen; each $R_5$, $R_7$, $R_{12}$, and $R_{14}$ is independently selected from hydrogen, alkyl, substituted alkyl, aryl, and substituted aryl; x is an integer from 1 to 3; y is an integer from 1 to 4; and z is an integer from 1 to 3. The compounds of Formula (I) may also be known as tetrahydrotetraazaacenes.

The term "alkyl" refers to a substituent composed entirely of carbon atoms and hydrogen atoms which is fully saturated and of the formula —$C_nH_{2n+1}$. The alkyl substituent may be linear, branched, or cyclic.

The term "alkenyl" refers to a substituent composed entirely of carbon atoms and hydrogen atoms which contains at least one carbon-carbon double bond.

The term "alkynyl" refers to a substituent composed entirely of carbon atoms and hydrogen atoms which contains at least one carbon-carbon triple bond.

A triple bond is not considered a double bond, and a double bond is not considered a triple bond. A substituent which contains a double bond and a triple bond should be considered an alkynyl substituent and not an alkenyl substituent.

The term "aryl" refers to an aromatic substituent composed entirely of carbon atoms and hydrogen atoms. When aryl is described in connection with a numerical range of carbon atoms, it should not be construed as including aromatic substituents which are substituted. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms).

The term "substituted" refers to at least one hydrogen atom on the named substituent being substituted with other functional groups, such as halogen, —CN, —$NO_2$, —COOH, —$SO_3H$, and —$SiR_3$ (where R is alkyl). An exemplary substituted alkyl group is a perhaloalkyl group, wherein one or more hydrogen atoms in an alkyl group are replaced with halogen atoms, such as fluorine, chlorine, iodine, and bromine. An exemplary substituted alkynyl group is 2-trimethylsilyl-ethynyl.

Generally, the alkyl, alkenyl, and alkynyl groups each independently contain from 1 to 30 carbon atoms. Similarly, the aryl groups independently contain from 6 to 30 carbon atoms.

In one specific embodiment of Formula (I), x, y, and z are 1; and $R_1$-$R_{14}$ are hydrogen. This compound is 5,7,12,14-tetrahydro-5,7,12,14-tetrahydroazapentacene, which may be abbreviated as TH-TAP and has the structure of Formula (1);

Formula (1)

In other specific embodiments of Formula (I), $R_2$ and $R_3$ are identical to each other, $R_9$ and $R_{10}$ are identical to each other, and $R_2$ is different from $R_9$. For example, $R_2$ and $R_3$ could be substituted (i.e. non-hydrogen), while $R_9$ and $R_{10}$ are hydrogen. As another example $R_9$ and $R_{10}$ could be substituted, while $R_2$ and $R_3$ are hydrogen.

In other embodiments of Formula (I), $R_2$, $R_3$, $R_9$, and $R_{10}$ are not hydrogen. In some embodiments, $R_2$, $R_3$, $R_9$, and $R_{10}$ are the same, and are not hydrogen.

In some embodiments of Formula (I), x and z are equal to each other. In others, y is from 2 to 4. In yet other versions, $R_5$, $R_7$, $R_{12}$, and $R_{14}$ are the same, and are not hydrogen. In other specific embodiments of Formula (I), x, y, and z are 1.

In specific embodiments, the compound is of Formula (II):

Formula (II)

wherein $R_2$, $R_3$, $R_9$, and $R_{10}$, are independently selected from hydrogen, alkyl, alkenyl, alkynyl, substituted alkyl, substituted alkenyl, substituted alkynyl, aryl, substituted aryl, and halogen; wherein $R_5$, $R_7$, $R_{12}$, and $R_{14}$ are independently selected from hydrogen, alkyl, substituted alkyl, aryl, and substituted aryl; and wherein at least one of $R_2$, $R_3$, $R_5$, $R_7$, $R_9$, $R_{10}$, $R_{12}$, or $R_{14}$ is not hydrogen.

In some specific embodiments of Formula (II), $R_2$ and $R_3$ are identical to each other; $R_9$ and $R_{10}$ are identical to each other; and $R_2$ is different from $R_9$. In further specific embodiment, $R_2$ and $R_9$ are not hydrogen.

In other specific embodiments of Formula (II), none of $R_2$, $R_3$, $R_5$, $R_7$, $R_9$, $R_{10}$, $R_{12}$, or $R_{14}$ are hydrogen; $R_2$ and $R_3$ are identical to each other; $R_9$ and $R_{10}$ are identical to each other; and $R_2$ is different from $R_9$.

In other versions of Formula (II), $R_5$, $R_7$, $R_{12}$, and $R_{14}$ are the same, and are not hydrogen.

In other embodiments, $R_2$, $R_3$, $R_9$, and $R_{10}$ are not hydrogen, or in other words are independently selected from alkyl, alkenyl, alkynyl, substituted alkyl, substituted alkenyl, substituted alkynyl, aryl, and substituted aryl. In alternate versions of Formula (II), $R_2$, $R_3$, $R_9$, and $R_{10}$ are the same, and are not hydrogen.

In other specific embodiments, the compound is of Formula (III):

Formula (III)

wherein $R_2$, $R_3$, $R_9$, and $R_{10}$ are independently selected from hydrogen, alkyl, alkenyl, alkynyl, substituted alkyl, substituted alkenyl, substituted alkynyl, aryl, and substituted aryl; and wherein at least one of $R_2$, $R_3$, $R_9$, or $R_{10}$ is not hydrogen.

In some specific embodiments of Formula (III), $R_2$ and $R_3$ are identical to each other; $R_9$ and $R_{10}$ are identical to each other; and $R_2$ is different from $R_9$. In a more specific versions, $R_2$ and $R_9$ are not hydrogen.

In other embodiments, $R_2$, $R_3$, $R_9$, and $R_{10}$ are not hydrogen, or in other words are independently selected from alkyl, alkenyl, alkynyl, substituted alkyl, substituted alkenyl, substituted alkynyl, aryl, and substituted aryl. In alternate versions of Formula (III), $R_2$, $R_3$, $R_9$, and $R_{10}$ are the same, and are not hydrogen.

In other specific embodiments, the compound is of Formula (IV):

Formula (IV)

wherein $R_5$, $R_7$, $R_{12}$, and $R_{14}$ are independently selected from alkyl, substituted alkyl, aryl, and substituted aryl.

In specific versions of Formula (IV), $R_5$, $R_7$, $R_{12}$, and $R_{14}$ are the same. In other specific versions, $R_5$ and $R_{14}$ are identical to each other; $R_7$ and $R_{12}$ are identical to each other; and $R_5$ is different from $R_7$.

Generally speaking, the R substituents are selected so as to increase the solubility of the compound, alter the chromophore properties and tune the semiconducting properties, affect the solid state packing, and/or improve the oxidative stability of the compound.

The small molecule semiconducting compounds of Formula (I) can be made by the condensation reaction of appropriate reactants. For example, 1,2-phenylene diamines can be reacted with 1,2,4,5-tetrahydroxybenzene to form the compound of Formula (1), as illustrated below:

Generally, these compounds can be formed by a process comprising reacting two molar units of at least one 1,2-diaminobenzene compound of Formula (A) with one molar unit of a 1,2,4,5-tetrahydroxybenzene compound of Formula (B):

Formula (A)

Formula (B)

wherein $R_a$, $R_b$, $R_c$, $R_d$, $R_e$, and $R_f$ are independently selected from the group consisting of hydrogen, alkyl, substituted alkyl, alkenyl, substituted alkenyl, alkynyl, substituted alkynyl, aryl, substituted aryl, heteroaryl, substituted heteroaryl, ketonyl, arylalkyl, and halogen; and R' and R" are independently selected from the group consisting of hydrogen, alkyl, substituted alkyl, aryl, and substituted aryl; and $R_g$, $R_h$, $R_i$, and $R_j$ are independently selected from the group consisting of hydrogen, alkyl, and substituted alkyl.

The term "ketonyl" refers to a substituent having a carbon atom double-bonded to an oxygen atom and single bonded to an alkyl or substituted alkyl group, i.e. —(C=O)—R. An exemplary ketonyl substituent is methylcarbonyl (—COCH$_3$).

The term "arylalkyl" refers to an aromatic substituent which is connected to an alkylene substituent. An alkylene substituent is composed of carbon atoms which are fully saturated, and has the ability to form a single bond with two different atoms. Arylalkyl groups can also be substituted. Exemplary arylalkyl substituents include benzyl (—CH$_2$—C$_6$H$_5$).

In some embodiments, the reaction occurs by heating a solid mixture of the two starting materials of Formulas (A) and (B) in an inert atmosphere, such as nitrogen (N$_2$) or argon.

In other embodiments, the diaminobenzene of Formula (A) and the tetrahydroxybenzene of Formula (B) are dissolved in a solvent and heated.

In embodiments, the diaminobenzene compound and tetrahydroxybenzene compound are heated at a temperature above 300° C., including from about 300° C. to about 500° C., including about 300° C. to about 450° C. for a period of time between about 30 seconds and about 10 minutes when mixed in the absence of a solvent. Such heating can be accomplished using a torch. Alternatively, the diaminobenzene compound and tetrahydroxybenzene compound are heated at a temperature between about 110° C. and about 250° C., including from about 150° C. to about 200° C. for a period of time between about 30 minutes and about 12 hours, when mixed in the absence of a solvent. When dissolved in a solvent, the diaminobenzene compound and tetrahydroxybenzene compound are heated at a temperature between about 80° C. and about 110° C. The diaminobenzene compound and tetrahydroxybenzene compound are heated for a period of time between about 30 minutes and about 12 hours. This heating can be done in an oven, for example.

As noted above, the diaminobenzene compound and tetrahydroxybenzene compound can be dissolved in a solvent prior to heating. Exemplary solvents include carboxylic acids such as acetic acid, methanoic acid, ethanoic acid, octadecanoic acid, propanoic acid, (Z)-9-octadecanoic acid, benzenecarboxylic acid, propanedioic acid, butanedioic acid, and the like, and combinations thereof; and polar, aprotic solvents such as NMP, DMF, DMA, DMSO, and the like, and combinations thereof.

After reaction, the tetraazapentacene compound can be washed with acetone or a variety of other solvents such as methanol, toluene, THF, and diethyl ether; and dried, for example in a vacuum oven. The drying typically occurs at a temperature of about 60° C. for a period of from about 8 hours to about 12 hours. The product can be further purified by sublimation or acid pasting.

Derivatives of TH-TAP may also be desirable. For example, substitutions on the A and E rings, i.e. the terminal phenyl rings, may aid solubility, extend the chromophore to tune the semiconductor properties, and/or affect the solid state packing. These substitutions occur when at least one of $R_a$, $R_b$, $R_c$, and $R_d$ in the compound of Formula (A) is not hydrogen. In particular embodiments, at least one of $R_a$, $R_b$, $R_c$, and $R_d$ is selected from alkyl, aryl, alkenyl, and alkynyl.

In other embodiments, the nitrogen atoms are substituted. Such a substitution may aid solubility, extend the chromophore to tune the semiconductor properties, affect the solid state packing, and/or improve the oxidative stability of the compound. These substitutions occur when at least one of R' and R" is not hydrogen. In particular embodiments, at least one of R' and R" is selected from substituted alkyl and substituted aryl.

Substitutions on the C ring, i.e. the internal phenyl ring, may also be desirable. These substitutions occur when at least one of $R_e$ and $R_f$ in the compound of Formula (B) is not hydrogen. In particular embodiments, at least one of $R_e$ and $R_f$ is selected from alkyl, aryl, alkenyl, and alkynyl.

Symmetrical tetrahydrotetraazapentacene derivatives can be prepared using two equivalents of the diaminobenzene compound of Formula (A) to react with the tetrahydroxybenzene compound of Formula (B), as illustrated in Reaction (1) below:

Reaction (1)

-continued

Reactions (2) and (3) may be utilized when different substitutions on the A and E rings are desired. First, as shown in Reaction (2), one equivalent of a first diaminobenzene is reacted with the tetrahydroxybenzene. Put another way, the molar ratio of the first diaminobenzene compound and the tetrahydroxybenzene compound is about 1:1.

Reaction (2)

Next, in Reaction (3), the intermediate product produced in Reaction (2) is reacted with a second diaminobenzene compound. The second diaminobenzene compound is different from the first diaminobenzene compound.

Reaction (3).

In Reaction (4), the C ring is substituted, i.e. one or both of $R_e$ and $R_f$ is not hydrogen. This result can be achieved by appropriate substitutions on the tetrahydroxybenzene compound.

Reaction (4)

In Reaction (5), one or more of the nitrogen atoms of the B and/or D rings is substituted. This result can be achieved by substituting one or both of the amine groups of the diaminobenzene.

Reaction (5)

When the nitrogen atom substituents are the same, symmetrical B and D ring derivatives are prepared. When the nitrogen atom substituents are different, a mixture of unsymmetrical regioisomers is prepared.

The concepts of the above Reactions (1)-(5) may be combined to produce compounds with substitutions at every position on the tetraazapentacene framework. Depending on the compound to be produced, adding a molar excess of the diaminobenzene compound ensures completion of the reaction. In embodiments, the molar ratio of the at least one diaminobenzene compound to the tetrahydroxybenzene compound is from 2:1 to about 2.5:1.

Compounds having substituents on the nitrogen atoms of the B and/or D rings can also be prepared by functionalizing TH-TAP. Generally speaking, N-substituted compounds of Formula (A) are formed by reacting TH-TAP with a sidechain-producing reactant to obtain an N-substituted TH-TAP compound. The sidechain-producing reactant reacts selectively with the nitrogen atoms, rather than any of the carbon atoms in the A, C, or E rings. For example, as shown in Reactions (6), (7), (8), and (9), N-substituted compounds can be obtained by an alkylation or cross-coupling reaction:

wherein in Reactions (6)-(8) each R is independently alkyl, substituted alkyl, aryl, substituted aryl, heteroaryl, or substituted heteroaryl, and in Reaction (9) R may also be trialkylsilyl. Please note the overall substituent on the nitrogen atom of Reaction (8) would be considered an alkenyl or substitutent alkenyl substituent. The overall substituent on the nitrogen atom of Reaction (9) would be considered an alkynyl or substituted alkynyl substituent.

Generally, the sidechain-producing reactant is of Formula (C):

$$X\text{-}L\text{-}R_{15} \qquad \text{Formula (C)}$$

where X is halogen or hydrogen; $R_{15}$ is selected from alkyl, substituted alkyl, alkenyl, substituted alkenyl, alkynyl, substituted alkynyl, aryl, substituted aryl, heteroaryl, substituted heteroaryl, ketonyl, and arylalkyl; and L is a divalent linkage. The term "divalent linkage" refers to any moiety which is able to form a single bond with two different atoms, joining those two different atoms together. Exemplary divalent linkages that may be useful in Formula (C) include carbonyl (—C(=O)—), a single bond (I.e. the formula collapses into X—$R_{15}$), ethenyl (—CH=CH—), and acetylenyl (—C≡C—).

In some embodiments, the sidechain-producing reactant is reduced to obtain the N-substituted TH-TAP compound. For example, in Reaction (10), TH-TAP is reacted with an acid chloride, which can provide N-substituted compounds having a ketonyl substituent. The resulting intermediate can be be reduced, if desired, to obtain alkyl or substituted alkyl substituents. Any suitable reducing agent may be used; $LiAlH_4$ is merely exemplary.

Reaction (10)

-continued or

N-substituted compounds with different substituents can be made by performing Reactions (6)-(10) sequentially with an excess of the TH-TAP compound compared to the sidechain-producing reagent, as desired.

The compounds of Formula (I) can be used as a semiconductor in the semiconducting layer of an electronic device, such as a thin-film transistor. The semiconducting layer may be formed from a semiconductor composition comprising the compound of Formula (I) and a polymeric binder. The polymer binder can be considered as forming a matrix within which the compound of Formula (I) is dispersed.

Exemplary polymer binders include polythiophenes, polystyrene, poly(methyl methacrylate), poly(N-vinylcarbazole), poly(α-methyl styrene), poly(4-methyl styrene), poly(vinyl cinnamate), a triarylamine polymer, a polysiloxane, and mixtures thereof.

The weight ratio of the compound of Formula (I) to the polymer binder may be from 2:1 to 3:4.

The semiconductor composition may further comprise a solvent in which the small molecule semiconductor of Formula (I) and the polymer binder are soluble. Exemplary solvents used in the solution may include DMSO, DMA, NMP, and the like.

An optional crosslinking agent and an optional catalyst may also be present in the semiconductor composition. Generally speaking, the crosslinking agent has at least two crosslinking groups, such as amino, hydroxyl, alkoxy, etc., which are capable of reacting with the functional groups on the amorphous molecular material to form a crosslinked network or matrix comprising the crosslinking agent or part of the crosslinking agent. Exemplary crosslinking agents include a melamine-formaldehyde resin, a phenol-formaldehyde resin, and 1,3,4,6-tetrakis(methoxylmethyl)glycoluril. The optional catalyst may be an acid catalyst, such as toluene sulfonic acid (TSA). When a photoacid generator, i.e. a compound that generates acid upon light irradiation, is used as the acid catalyst, the semiconducting layer can be patterned into the desired structure. Such photoacid generators are known in the art, and include bis(4-tert-butylphenyl)iodonium perfluoro-1-butanesulfonate, bis(4-tert-butylphenyl)iodonium p-toluenesulfonate, etc. The optional catalyst may also be a base. Exemplary base catalysts include organoamines such as triethylamine, phosphanes, carbonyl, nitrosyl, N-heterocyclic carbine ligands, imidazolidinone and pyrrolidine derivatives, and the like.

In embodiments, the semiconductor composition comprising the small molecule semiconductor and the polymer binder has a viscosity of from 1 centipoise (cps) to 30 cps, or more desirably a viscosity of from 1 cps to 20 cps.

The semiconducting layer may be formed in an electronic device using conventional processes known in the art. In embodiments, the semiconducting layer is formed using solution depositing techniques. Exemplary solution depositing techniques include spin coating, blade coating, rod coating, dip coating, screen printing, ink jet printing, stamping, stencil printing, screen printing, gravure printing, flexography printing, and the like. Exemplary electronic devices include thin film transistors, photovoltaic cells, sensors, memory, and light emitting diodes. The semiconducting layer may also be vacuum deposited.

Figure 1:
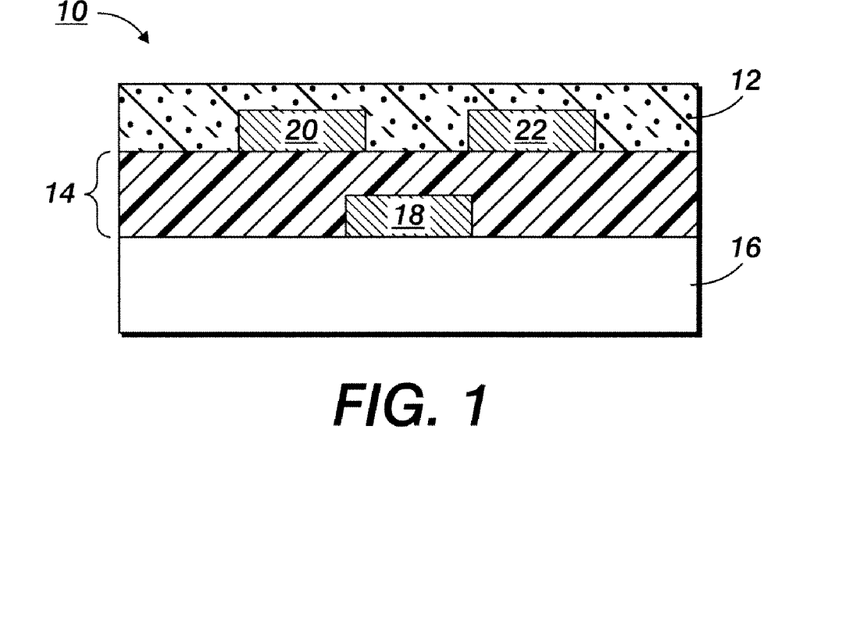
FIG. 1 is an exemplary embodiment of an OTFT of the present disclosure.

FIG. 1 illustrates a first organic thin film transistor (OTFT) embodiment or configuration. The OTFT 10 comprises a substrate 20 in contact with the gate electrode 30 and a dielectric layer 40. Although here the gate electrode 30 is depicted within the substrate 20, this is not required. However, of some importance is that the dielectric layer 40 separates the gate electrode 30 from the source electrode 50, drain electrode 60, and the semiconducting layer 70. The source electrode 50 contacts the semiconducting layer 70. The drain electrode 60 also contacts the semiconducting layer 70. The semiconducting layer 70 runs over and between the source and drain electrodes 50 and 60. An optional interfacial layer 80 is located between dielectric layer 40 and semiconducting layer 70.

Figure 2:
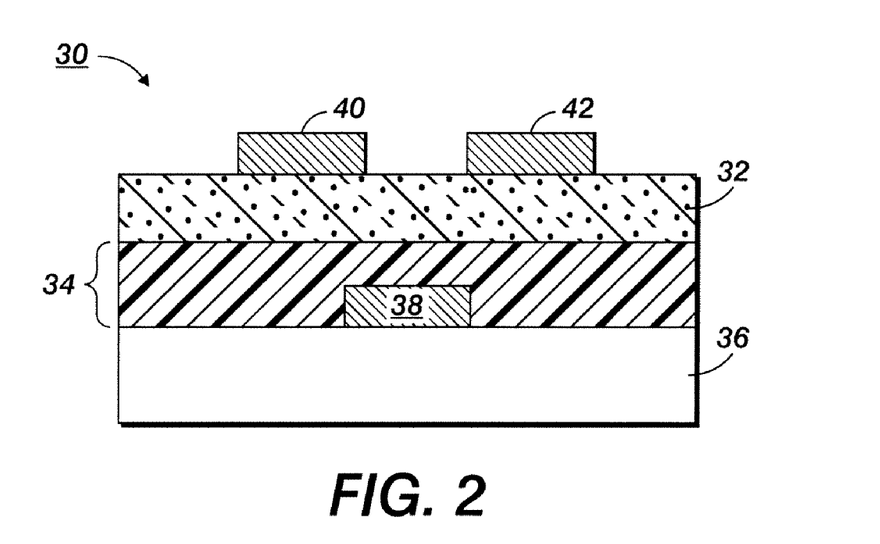
FIG. 2 is a second exemplary embodiment of an OTFT of the present disclosure.

FIG. 2 illustrates a second OTFT embodiment or configuration. The OTFT 10 comprises a substrate 20 in contact with the gate electrode 30 and a dielectric layer 40. The semiconducting layer 70 is placed over or on top of the dielectric layer 40 and separates it from the source and drain electrodes 50 and 60. Optional interfacial layer 80 is located between dielectric layer 40 and semiconducting layer 70.

Figure 3:
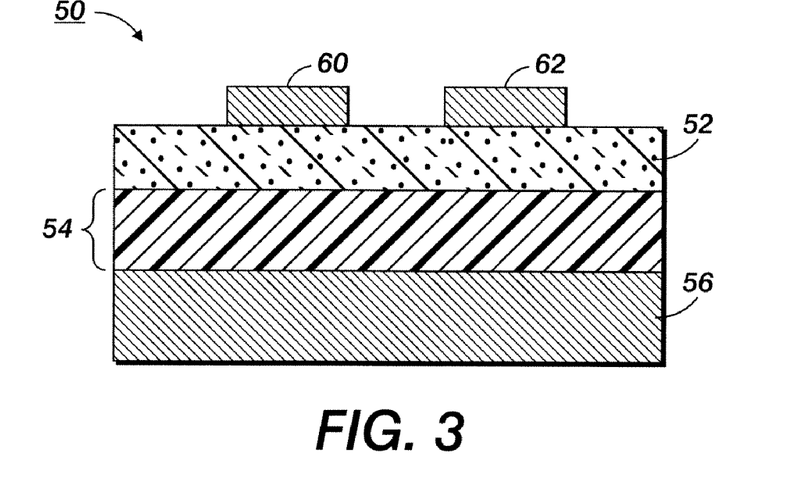
FIG. 3 is a third exemplary embodiment of an OTFT of the present disclosure.

FIG. 3 illustrates a third OTFT embodiment or configuration. The OTFT 10 comprises a substrate 20 which also acts as the gate electrode and is in contact with a dielectric layer 40. The semiconducting layer 70 is placed over or on top of the dielectric layer 40 and separates it from the source and drain electrodes 50 and 60. Optional interfacial layer 80 is located between dielectric layer 40 and semiconducting layer 70.

Figure 4:
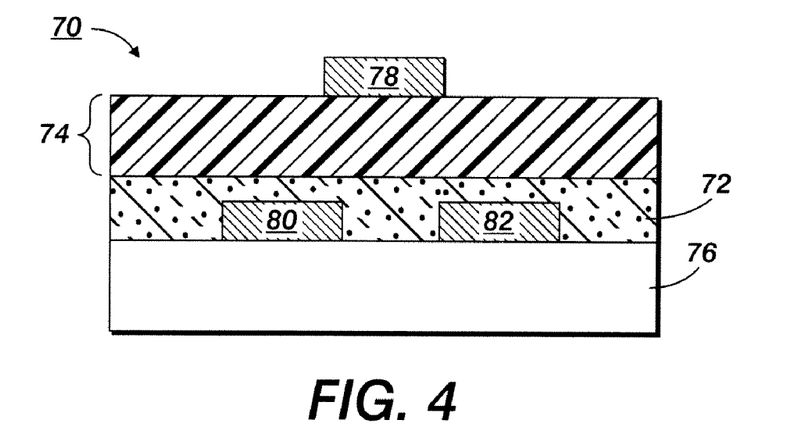
FIG. 4 is a fourth exemplary embodiment of an OTFT of the present disclosure.

FIG. 4 illustrates a fourth OTFT embodiment or configuration. The OTFT 10 comprises a substrate 20 in contact with the source electrode 50, drain electrode 60, and the semiconducting layer 70. The semiconducting layer 70 runs over and between the source and drain electrodes 50 and 60. The dielectric layer 40 is on top of the semiconducting layer 70. The gate electrode 30 is on top of the dielectric layer 40 and does not contact the semiconducting layer 70. Optional interfacial layer 80 is located between dielectric layer 40 and semiconducting layer 70.

The semiconducting layer formed using the semiconductor composition can be from about 5 nanometers to about 1000 nanometers deep, including from about 20 to about 100 nanometers in depth. In certain configurations, such as the configurations shown in FIGS. 1 and 4, the semiconducting layer completely covers the source and drain electrodes.

A thin film transistor generally includes a substrate, an optional gate electrode, source electrode, drain electrode, and a dielectric layer in addition to the semiconducting layer.

The substrate may be composed of materials including but not limited to silicon, glass plate, plastic film or sheet. For structurally flexible devices, plastic substrate, such as for example polyester, polycarbonate, polyimide sheets and the like may be preferred. The thickness of the substrate may be from about 10 micrometers to over 10 millimeters with an exemplary thickness being from about 50 to about 100 micrometers, especially for a flexible plastic substrate and from about 0.5 to about 10 millimeters for a rigid substrate such as glass or silicon.

The dielectric layer generally can be an inorganic material film, an organic polymer film, or an organic-inorganic composite film. Examples of inorganic materials suitable as the dielectric layer include silicon oxide, silicon nitride, aluminum oxide, barium titanate, barium zirconium titanate and the like. Examples of suitable organic polymers include polyesters, polycarbonates, poly(vinyl phenol), polyimides, polystyrene, polymethacrylates, polyacrylates, epoxy resin and the like. The thickness of the dielectric layer depends on the dielectric constant of the material used and can be, for example, from about 10 nanometers to about 500 nanometers. The dielectric layer may have a conductivity that is, for example, less than about $10^{-12}$ Siemens per centimeter (S/cm). The dielectric layer is formed using conventional processes known in the art, including those processes described in forming the gate electrode.

In the present disclosure, the dielectric layer may be surface modified with a surface modifier. Exemplary surface modifiers include hexamethyldisilazane (HMDS) and octyltrichlorosilane (OTS-8). The semiconducting layer can be directly contacted with this modified dielectric layer surface. The contact may be complete or partial. This surface modification can also be considered as forming an interfacial layer between the dielectric layer and the semiconducting layer.

The gate electrode is composed of an electrically conductive material. It can be a thin metal film, a conducting polymer film, a conducting film made from conducting ink or paste, or the substrate itself, for example heavily doped silicon. Examples of gate electrode materials include but are not restricted to aluminum, gold, silver, chromium, indium tin oxide, conductive polymers such as polystyrene sulfonate-doped poly(3,4-ethylenedioxythiophene) (PSS-PEDOT), and conducting ink/paste comprised of carbon black/graphite. The gate electrode can be prepared by vacuum evaporation, sputtering of metals or conductive metal oxides, conventional lithography and etching, chemical vapor deposition, spin coating, casting or printing, or other deposition processes. The thickness of the gate electrode ranges for example from about 10 to about 200 nanometers for metal films and from about 1 to about 10 micrometers for conductive polymers. Typical materials suitable for use as source and drain electrodes include those of the gate electrode materials such as aluminum, gold, silver, chromium, zinc, indium, conductive metal oxides such as zinc-gallium oxide, indium tin oxide, indium-antimony oxide, conducting polymers and conducting inks. Typical thicknesses of source and drain electrodes are, for example, from about 40 nanometers to about 1 micrometer, including more specific thicknesses of from about 100 to about 400 nanometers.

Typical materials suitable for use as source and drain electrodes include those of the gate electrode materials such as gold, silver, nickel, aluminum, platinum, conducting polymers, and conducting inks. In specific embodiments, the electrode materials provide low contact resistance to the semiconductor. Typical thicknesses are about, for example, from about 40 nanometers to about 1 micrometer with a more specific thickness being about 100 to about 400 nanometers. The OTFT devices of the present disclosure contain a semiconductor channel. The semiconductor channel width may be, for example, from about 5 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

The source electrode is grounded and a bias voltage of, for example, about 0 volt to about 80 volts is applied to the drain electrode to collect the charge carriers transported across the semiconductor channel when a voltage of, for example, about +10 volts to about −80 volts is applied to the gate electrode. The electrodes may be formed or deposited using conventional processes known in the art.

If desired, a barrier layer may also be deposited on top of the TFT to protect it from environmental conditions, such as light, oxygen and moisture, etc. which can degrade its electrical properties. Such barrier layers are known in the art and may simply consist of polymers.

The various components of the OTFT may be deposited upon the substrate in any order. Generally, however, the gate electrode and the semiconducting layer should both be in contact with the gate dielectric layer. In addition, the source and drain electrodes should both be in contact with the semiconducting layer. The phrase "in any order" includes sequential and simultaneous formation. For example, the source electrode and the drain electrode can be formed simultaneously or sequentially. The term "on" or "upon" the substrate refers to the various layers and components with reference to the substrate as being the bottom or support for the layers and components which are on top of it. In other words, all of the components are on the substrate, even though they do not all directly contact the substrate. For example, both the dielectric layer and the semiconductor layer are on the substrate, even though one layer is closer to the substrate than the other layer. The resulting TFT has good mobility and good current on/off ratio.

The following examples illustrate compounds and electronic devices made according to the methods of the present disclosure. The examples are merely illustrative and are not intended to limit the present disclosure with regard to the materials, conditions, or process parameters set forth therein. All parts are percentages by weight unless otherwise indicated.

EXAMPLES

Example 1

5,7,12,14-tetrahydrotetraazapentacene, corresponding to that of Formula (1), was prepared.

1,2-Phenylene diamine (8.37 grams, 77 mmol, 2.2 equivalents) and 1,2,4,5-tetrahydroxybenzene (5.0 grams, 35.2 mmol, 1 equivalent) were ground together using a mortar and pestle and transferred to an amber jar and purged thoroughly with argon. The jar was sealed and placed in a 180° C. oven for 4 hours. The crude product was purified by train vacuum sublimation (sample furnace temperature 360° C.) to afford the product as a dark purple (black) solid with a metallic green shine.

The product had a sublimation temperature of approximately 350° C. The product was sparingly soluble in DMSO, DMF, NMP, and THF; and had low to no solubility in alcohols and hydrocarbons. Solvatochromic behavior was also observed; in DMSO a bright fluorescent red/pink color was observed. The product could also be protonated with strong acids (HCl, $H_2SO_4$) to form a deep red-colored solution. Alternatively, the product could be deprotonated with strong bases (NaOH) to form a deep blue-colored solution.

In DSC, no thermal event was observed up to 350° C.

In TGA, there was less than 1% loss at 300° C.; 4% loss at 450° C.; and major product loss began around 550° C.

A molecular weight of 286.1218 Da was calculated. Using MALDI-TOF mass spectrometry, a molecular weight of 285.8100 Da was observed.

Example 2

TH-TAP can also be prepared as described below. 1,2-Phenylene diamine (799 milligrams, 7.39 mmol, 2.1 eq) and pyrocatechol (500 mg, 3.52 mmol, 1 eq) were ground together using a mortar and pestle and transferred to an amber jar and purged thoroughly with Argon. The amber jar was clamped by the lid and heated in an oven at 180° C. for 4 hours. A green residue was present on the side of the vial with a dark (black) residue at the bottom. The sample was purified by train vacuum sublimation with a first zone (sample) at 360° C. and a second zone at 340° C. to afford a metallic green solid.

Example 3

2,3,9,10-tetramethyl-5,7,12,14-tetrahydrotetraazapentacene was prepared. This compound is illustrated as Formula (2) below:

Formula (2)

1,2,4,5-tetrahydroxybenzene (2.0 grams, 14.1 mmol) and 4,5-dimethyl-1,2-phenylenediamine (3.83 grams, 28.2 mmol) were ground together with a mortar and pestle, and placed in a tightly sealed vial under an argon atmosphere. The vial was heated in a 180° C. oven for 4 hours, then opened to air and allowed to cool. The resulting material was washed with acetone several times, filtered, and dried.

A portion (2 grams) of the isolated sample was slowly added to trifluoroacetic acid (175 mL) over a 30 minute period and allowed to dissolve for 45 minutes. The resulting solution was filtered to remove insoluble impurities. The filtrate (a dark blue mixture) was added slowly to ice-cold deionized water (700 mL). The resulting precipitate was collected by filtration, reslurried in deioized water, filtered, and dried in a vacuum oven at 50° C. to afford the product as a black-purple solid (1.52 grams).

Example 4

9,10-dimethyl-5,7,12,14-tetrahydroazapentacene was prepared. This compound is illustrated as Formula (3) below:

Formula (3)

1,2-Phenylene diamine (761 mg, 7.04 mmol, 1 eq) and 1,2,4,5-tetrahydroxybenzene (1.00 grams, 7.04 mmol, 1 eq) were ground together using a mortar and pestle and transferred to an amber jar and purged thoroughly with Ar. The jar was sealed and placed in a 180° C. oven for 3 hours. The jar was cooled to room temperature and the material was blended with 4,5-dimethylphenylenediamine (958 mg, 7.04 mmol, 1 eq) in a mortar and pestle. The jar was purged with Argon, sealed, and placed in a 180° C. oven for 3 hours. The sample was removed from the oven and cooled to room temperature. The sample was a mass of black (shimmery green) solid. The sample weighed 2.03 grams indicating a yield of 92%.

Example 5

A compound of Formula (4) was prepared:

Formula (4)

1,2,4,5-tetrahydroxybenzene (158 mg, 1.11 mmol, 1.0 eq.) was ground to a fine powder using a mortar and pestle and then added to a glass vial containing N,N'-dimethyl-o-phenylenediamine (303 mg, 2.22 mmol, 2.0 eq.). The vial was flushed thoroughly with argon, sealed, and then heated slightly under a flame gun to make a homogeneous solid. The reaction was heated to 180° C. for 4 hours to afford a brown solid.

Example 6

A compound of Formula (5) was prepared:

Formula (5)

To a vial containing argon-degassed acetic acid (2.5 mL) was added N,N'-diphenyl-o-phenylenediamine (131 mg, 0.50 mmol, 2.0 eq.) followed by 1,2,4,5-tetrahydroxybenzene (35.6 mg, 0.25 mmol, 1.0 eq.). The result was a pink suspension. The reaction was heated to reflux for 5 days under an argon atmosphere. All solid initially dissolved upon heating to form a clear solution. The solution gradually darkened over the course of 5 days, and a dark precipitate formed. The reaction was completely black after 5 days.

The compounds and devices of the present disclosure have been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

What is claimed is:

1. A compound of Formula (I):

Formula (I)

wherein each $R_1$, $R_2$, $R_3$, $R_4$, $R_6$, $R_8$, $R_9$, $R_{10}$, $R_{11}$, and $R_{13}$ is independently selected from hydrogen, alkyl, alkenyl, alkynyl, substituted alkyl, substituted alkenyl, substituted alkynyl, aryl, substituted aryl, and halogen; each $R_5$, $R_7$, $R_{12}$, and $R_{14}$ is independently selected from hydrogen, alkyl, substituted alkyl, aryl, and substituted aryl; x is an integer from 1 to 3; y is an integer from 1 to 4; and z is an integer from 1 to 3.

2. The compound of claim 1, wherein x, y, and z are 1 and $R_1$-$R_{14}$ are hydrogen.

3. The compound of claim 1, wherein $R_2$ and $R_3$ are identical to each other, $R_9$ and $R_{10}$ are identical to each other, and $R_2$ is different from $R_9$.

4. The compound of claim 1, wherein $R_2$, $R_3$, $R_9$, and $R_{10}$ are not hydrogen.

5. The compound of claim 4, wherein $R_2$, $R_3$, $R_9$, and $R_{10}$ are the same.

6. The compound of claim 1, wherein the compound is of Formula (II):

Formula (II)

wherein $R_2$, $R_3$, $R_9$, and $R_{10}$, are independently selected from hydrogen, alkyl, alkenyl, alkynyl, substituted alkyl, substituted alkenyl, substituted alkynyl, aryl, substituted aryl, and halogen; wherein $R_5$, $R_7$, $R_{12}$, and $R_{14}$ are independently selected from alkyl, substituted alkyl, aryl, and substituted aryl; and wherein at least one of $R_2$, $R_3$, $R_5$, $R_7$, $R_9$, $R_{10}$, $R_{12}$, or $R_{14}$ is not hydrogen.

7. The compound of claim 1, wherein the compound is of Formula (III):

Formula (III)

wherein $R_2$, $R_3$, $R_9$, and $R_{10}$ are independently selected from hydrogen, alkyl, alkenyl, alkynyl, substituted alkyl, substituted alkenyl, substituted alkynyl, aryl, substituted aryl, and halogen; and wherein at least one of $R_2$, $R_3$, $R_9$, or $R_{10}$ is not hydrogen.

8. The compound of claim 7, wherein $R_2$ and $R_3$ are identical to each other, $R_9$ and $R_{10}$ are identical to each other, and $R_2$ is different from $R_9$.

9. The compound of claim 1, wherein the compound is of Formula (IV):

Formula (IV)

wherein $R_5$, $R_7$, $R_{12}$, and $R_{14}$ are independently selected from alkyl, substituted alkyl, aryl, and substituted aryl.

10. The compound of claim 9, wherein $R_5$, $R_7$, $R_{12}$, and $R_{14}$ are the same.

11. The compound of claim 9, wherein $R_5$ and $R_{14}$ are identical to each other; $R_7$ and $R_{12}$ are identical to each other; and $R_5$ is different from $R_7$.

12. A thin film transistor, comprising:
a substrate; and
a semiconducting layer on the substrate, the semiconducting layer comprising a tetrahydrotetraazaacene of Formula (I):

Formula (I)

wherein each $R_1$, $R_2$, $R_3$, $R_4$, $R_6$, $R_8$, $R_9$, $R_{10}$, $R_{11}$, and $R_{13}$ is independently selected from hydrogen, alkyl, alkenyl, alkynyl, substituted alkyl, substituted alkenyl, substituted alkynyl, aryl, substituted aryl, and halogen; each $R_5$, $R_7$, $R_{12}$, and $R_{14}$ is independently selected from hydrogen, alkyl, substituted alkyl, aryl, and substituted aryl; x is an integer from 1 to 3; y is an integer from 1 to 4; and z is an integer from 1 to 3.

13. The transistor of claim 12, wherein x, y, and z are 1 and $R_1$-$R_{14}$ are hydrogen.

14. The transistor of claim 12, wherein x and z are equal to each other.

15. The transistor of claim 12, wherein y is from 2 to 4.

16. The transistor of claim 12, wherein $R_5$, $R_7$, $R_{12}$, and $R_{14}$ are the same.

17. The transistor of claim 12, wherein $R_2$ and $R_3$ are identical to each other, $R_9$ and $R_{10}$ are identical to each other, and $R_2$ is different from $R_9$.

18. The transistor of claim 12, wherein the tetrahydrotetraazaacene is of Formula (II):

Formula (II)

wherein $R_2$, $R_3$, $R_9$, and $R_{10}$, are independently selected from hydrogen, alkyl, alkenyl, alkynyl, substituted alkyl, substituted alkenyl, substituted alkynyl, aryl, substituted aryl, and halogen; wherein $R_5$, $R_7$, $R_{12}$, and $R_{14}$ are independently selected from hydrogen, alkyl, substituted alkyl, aryl, and substituted aryl; and wherein at least one of $R_2$, $R_3$, $R_5$, $R_7$, $R_9$, $R_{10}$, $R_{12}$, or $R_{14}$ is not hydrogen.

19. The transistor of claim 12, wherein the tetrahydrotetraazaacene is of Formula (III):

Formula (III)

wherein $R_2$, $R_3$, $R_9$, and $R_{10}$ are independently selected from hydrogen, alkyl, alkenyl, alkynyl, substituted alkyl, substituted alkenyl, substituted alkynyl, aryl, and substituted aryl; and wherein at least one of $R_2$, $R_3$, $R_9$, or $R_{10}$ is not hydrogen.

20. The transistor of claim 12, wherein the tetrahydrotetraazaacene is of Formula (IV):

Formula (IV)

wherein $R_5$, $R_7$, $R_{12}$, and $R_{14}$ are independently selected from alkyl, substituted alkyl, aryl, and substituted aryl.

* * * * *